United States Patent [19]

Wiezer et al.

[11] 4,234,471

[45] Nov. 18, 1980

[54] NOVEL POLYALKYL-PIPERIDINE POLYMERS, THEIR PREPARATION AND USE

[75] Inventors: Hartmut Wiezer, Gersthofen; Helmut Korbanka, Adelsried; Gerhard Pfahler, Augsburg, all of Fed. Rep. of Germany

[73] Assignee: Hoechst Aktiengesellschaft, Fed. Rep. of Germany

[21] Appl. No.: 73,540

[22] Filed: Sep. 7, 1979

[30] Foreign Application Priority Data

Sep. 13, 1978 [DE] Fed. Rep. of Germany ...... 2839711

[51] Int. Cl.$^3$ .................. C08K 5/16; C08G 12/26
[52] U.S. Cl. .................. 260/45.8 N; 260/45.9 NC; 525/398; 528/266; 546/184; 546/188; 546/190

[58] Field of Search ............ 260/45.8 R, 45.8 N, 260/45.9 R, 45.9 N; 525/398; 528/266; 546/184, 188, 190

[56] References Cited

U.S. PATENT DOCUMENTS

| | | | |
|---|---|---|---|
| 4,139,520 | 2/1979 | Ramey et al. | 260/45.8 N |
| 4,154,722 | 5/1979 | Malherbe et al. | 260/45.8 N |

*Primary Examiner*—Lucille M. Phynes
*Attorney, Agent, or Firm*—Connolly and Hutz

[57] ABSTRACT

By reacting polyalkyl-piperidones-4 with the 0.5- to 1.1-molar amount of formaldehyde in the presence of an aliphatic monoalcohol at 50° to 180° C., polymers of a polymerization degree of from 2 to about 200 are obtained, which may be hydrogenated or partially hydrogenated. Especially in this form, they are suitable as light stabilizers for synthetic polymers and as intermediate products for the preparation of other stabilizers for plastic materials.

4 Claims, No Drawings

NOVEL POLYALKYL-PIPERIDINE POLYMERS, THEIR PREPARATION AND USE

It is known that polyalkyl-piperidones-2 of the formula (I), in which $R^2=R^3=H$ and $R^4=CH_3$, are condensed with the 2- to 4-fold molar amount of aqueous formaldehyde under weakly basic conditions and at low temperatures to yield a spiro compound (German Offenlegungsschrift No. 2 731 378 and references cited therein).

Surprisingly, there has now been found that, under similar reaction conditions, but in a medium of higher basicity and by reducing the formaldehyde amount, entirely different reaction products are obtained, that is, polymers containing from 2 to about 200 polyalkyl-piperidone units.

The invention relates therefore to a process for the preparation of such polymers, these novel polymers as such, and their use as light stabilizers for synthetic polymer compositions.

The process of the invention for the preparation of polyalkyl-piperidine/formaldehyde polymers comprises reacting a polyalkyl-piperidone-4 of the formula (I)

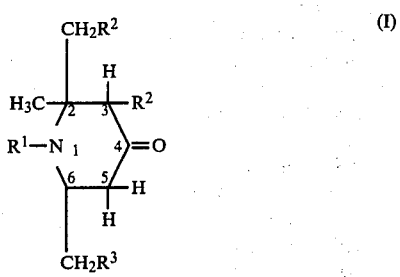

in which
  $R^1$ is hydrogen, oxygen, $C_1$–$C_{12}$-alkyl, preferably hydrogen, oxygen or $C_1$–$C_4$-alkyl, especially hydrogen;
  $R^2$ and $R^3$ are either identical and represent hydrogen or a $C_1$–$C_5$-alkyl group, preferably hydrogen or a methyl group, especially hydrogen; $R^4$ being a methyl group in this case; or
  $R^2$ is hydrogen or $C_1$–$C_5$-alkyl, preferably hydrogen or methyl, especially hydrogen; and
  $R^3$ and $R^4$ together with the carbon atoms linked to them form a $C_5$- or $C_6$-cycloalkyl group, or a group of the formula

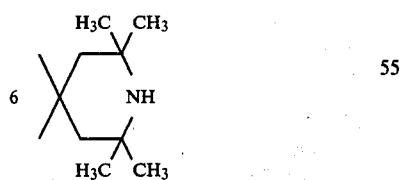

with the 0.5- to 1.1-fold molar amount of paraformaldehyde at a temperature of from 50° to 180° C. in the presence of an aliphatic $C_1$–$C_{10}$-monoalcohol and of an alkaline base, and subsequently optionally hydrogenating the product obtained.

Especially preferred are those polymers which are prepared on the basis of 2,2,6,6-tetramethyl-piperidone-4.

It was not to be expected at all that the reaction would proceed in this manner; on the contrary, it could be assumed that also in this case the spiro compounds known from the literature would be formed with, however, low yields. Therefore, the present results are all the more surprising.

The novel polyalkyl-piperidine polymers are characterized by the following structural formula (II)

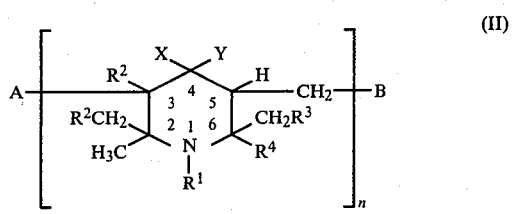

the symbols of which have the following meanings:
  X and Y together are oxygen, or are different and represent each hydrogen or a hydroxyl group in this case;
  $R^1$ is hydrogen, oxygen or $C_1$–$C_{12}$-alkyl, preferably hydrogen, oxygen or $C_1$–$C_4$-alkyl, especially hydrogen;
  $R^2$ and $R^3$ are either identical and represent each hydrogen or a $C_1$–$C_5$-alkyl group, preferably hydrogen or a methyl group, especially hydrogen; $R^4$ being a methyl group in this latter case; or
  $R^2$ is hydrogen or $C_1$–$C_5$-alkyl, preferably hydrogen or methyl; and
  $R^3$ and $R^4$ together with the carbon atoms linked to them are a $C_5$- or $C_6$-cycloalkyl group or a group of the formula

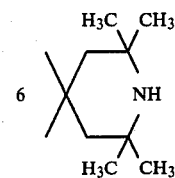

The terminal group
  A is hydrogen or a hydroxymethylene group.
  A and $R^2$, in the case where $R^2$ is hydrogen, form a methylene group when water is split off from A=hydroxymethylene and $R^2$.
  B is likewise a terminal group and represents hydrogen or a hydroxyl group, or a group of the formula (III)

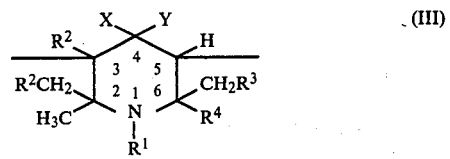

in which $R^1$ through $R^4$, X and Y are as defined above. The bond may be established via the carbon atom 3 or 5; the bond remaining free is saturated by H in this case.

In the case where B is a hydroxyl group, a $CH_2$ group may be formed by splitting-off of water, which $CH_2$ group is linked in this case to the polyalkyl-piperidine ring by means of a double bond.

n is a number of from 2 to 200, preferably 1 to 70, especially 2 to 30.

None of the hydrogen atoms in 3- and 5-position of the piperidone according to the formula (I) is preferred, so that the individual piperidone rings may be linked in 5,5-, 3,5- or 3,3-position.

The polyalkyl-piperidine polymers of the formula (II), in which X and Y together are oxygen, are prepared by condensation of 1 mol each of a compound of the formula (I) with the 0.5- to 1.1-fold molar amount of paraformaldehyde, with the use of catalytic amounts of alkaline bases.

Operations are as follows: the polyalkyl-piperidone of the formula (I) in a 0.2- to 10-fold, preferably 0.5 to 5-fold, and especially 0.5 to 2-fold amount of a $C_1$–$C_{10}$-alcohol is introduced into the vessel, and a solution of paraformaldehyde in the 3- to 10-fold, preferably 5- to 10-fold, especially 5- to 8-fold, amount by weight of the same alcohol, to which from 1 to 10, preferably 1 to 5, weight % relative to the polyalkyl-piperidone of the formula (I), of the alkaline base have been added as catalyst, are then fed in either at once, or in dosed quantities within up to 5 hours. The reaction temperature may be in a range of from 50° to 180°, preferably 70° to 150°, and especially 90° to 150° C. While maintaining the temperature chosen, the reaction is then allowed to continue for a further 5 to 50, preferably 10 to 20, hours.

By alkaline bases, there are to be understood alkali metal hydroxides such as sodium, potassium, lithium hydroxide, or alkali metal alcoholates such as sodium methylate, sodium ethylate, potassium isopropylate, or potassium tert.-butylate. Suitable solvents are above all methanol, ethanol, isopropanol, butanol and hexanol.

The polymerization rate which can be obtained depends on the temperature and the basicity of the catalysts. The higher the temperature and basicity of the catalyst, the higher the polymerization degree.

The compounds of the formula (II), where X is hydrogen and Y is hydroxyl, are obtained by reduction of those where X and Y together are oxygen according to hydrogenation methods known from the literature [H. Hörmann, Angew. Chem. 68 (1956), 601, E. Schenker, Angew. Chem. 73 (1961), 81, W. G. Brown, Org. Reactions 6 (1951), 469–510, Houben-Weyl, vol. IV/2, pp. 303–312, 318–328 (1955)].

By incomplete hydrogenation, polyalkyl piperidine polymers having keto and hydroxy groups in the same molecule can be obtained. Hydrogenation in this case is carried out as follows: the keto group-containing piperidine polymer is dissolved in the 1.5- to 10-fold amount by weight of absolute ethanol, 1 to 2.0 equivalents of $NaBH_4$ are added, and the batch is agitated for 20 to 60 hours at room temperature. Subsequently, it is poured for hydrolysis into the 5- to 10-fold amount of water, and the hydrogenation product is suction-filtered. All polymers obtained, either hydrogenated or not, can be purified by reprecipitation.

The novel polyalkyl-piperidine polymers are scarecely volatile compounds which, especially in the form of their hydrogenation products, are very good light stabilizers for synthetic polymers; they are, however, suitable above all for the preparation of other high-quality stabilizers for plastic materials.

Because of the indicated combination of stabilizing activity and low volatility, the compounds of the invention are of considerable technical importance, since for many applications, the hitherto known light stabilizers do not meet the corresponding requirements. These generally low molecular weight compounds are very easily volatile at the elevated processing temperatures of more than 250° C. in many cases. The consequences are reduced activity due to stabilizer losses, and processing troubles due to annoying vapors. Polymer stabilizers, too, may have these disadvantages, when the polymer chains tend to cracking at the processing temperatures of the synthetic polymer to be stabilized. Surprisingly, despite the large amount of polar groups contained therein, the novel polyalkyl-piperidine polymers are not affected by all these disadvantages, and they are very well compatible with the synthetic polymers to be stabilized.

The products in accordance with this invention are suitable for stabilizing-halogen free and halogen-containing homo- and copolymers, in particular homopolymers of olefins, dienes and styrene, for example polyethylene of low and high density, polypropylene, polystyrene, polybutadiene and polyisoprene, copolymers of olefins, dienes and styrene with one another or with other olefinically unsaturated monomers, such as ethylene-propylene copolymers, ethylene-butene copolymers, styrene-butadiene copolymers, ethylene-vinyl acetate copolymers and acrylonitrile-butadiene-styrene copolymers, homopolymers of vinyl chloride and vinylidene chloride and copolymers of these monomers with one another and with other olefinically unsaturated monomers. There are also to be included polyurethanes, polyacetals, polyesters, polyamides, polyacrylates, and epoxy resins. Preference is given to poly-α-olefins, such as polyethylenes and especially polypropylenes.

The novel stabilizing polymers are incorporated into the polymer compositions according to methods that are generally common. Alternatively, it is also possible to mix a solution, suspension or emulsion of the stabilizer directly with the polymer, or with a solution, suspension or emulsion of the same, and to eliminate the solvent thereafter.

The stabilizers of the invention may be used alone or in admixture with one or several of the stabilizers which are common in the processing of plastic materials, such as antioxidants on the basis of phenol and sulfide, UV-absorbers and light protecting agents, phosphite stabilizers, metal compounds, epoxy stabilizers and polyhydric alcohols. In the plastic compositions to be stabilized there may also be present flame-proofing agents and pigments, dyestuffs, antistatic agents and fillers, such as glass fibers.

Examples for appropriate antioxidants are those of the type of the sterically hindered phenols, such as 2,6-di-t.butyl-p-cresol, 2,6-di-octadecyl-p-cresol, 4,4'-butylidene-bis-(2,6-di-t.butyl-phenol), 4,4'-thio-bis-(2-t.butyl-5-methyl-phenol), phenolic triazine compounds, thiodipropionic acid esters of fatty alcohols, dioctadecyl sulfide and disulfide.

The UV-absorbers and light protecting agents include, for example, 2-(2'-hydroxyphenyl)-benzotriazoles, such as 2-(2'-hydroxy-5'-methylphenyl)-benzotriazole, 2-hydroxybenzophenones, such as 2-hydroxy-4-octoxy-benzophenone, stabilizers of the group of the salicylates, such as octylphenyl salicylate, nickel chelates, oxalic acid diamides and sterically hindered piperidine compounds.

As phosphites there are to be mentioned trisnonylphenyl phosphite, trislauryl phosphite or esters of pentaerythritol phosphite.

By metal compounds known as stabilizers there are to be understood: Calcium, barium, strontium, zinc, cadmium, magnesium, aluminum and lead soaps of aliphatic carboxylic acids or hydroxycarboxylic acids having from about 12 to 32 carbon atoms, salts of the aforesaid metals with aromatic carboxylic acids, such as benzoates or salicylates, and (alkyl-)phenolates of these metals, and also organo-tin compounds such as, for example, dialkyltin thioglycolates and carboxylates.

Known epoxy stabilizers are, for example, epoxidized higher fatty acids, such as epoxidized soy bean oil, tall oil, linseed oil or epoxidized butyl oleate, and also epoxides of long-chain olefins.

Polyhydric alcohols may be, for example, pentaerythritol, trimethylolpropane, sorbitol or mannitol, i.e. preferably alcohols having 5 or 6 carbon atoms and from 3 to 6 OH-groups.

An effective stabilizer combination for poly-α-olefins such as, for example, high, medium and low pressure polymers of $C_2$- to $C_4$-α-olefins, especially polyethylene and polypropylene or copolymers of such α-olefins, consists, calculated on 100 parts by weight of polymer, for example, of from 0.01 to 5 parts by weight of one of the stabilizers to be used in accordance with the invention, optionally of from 0.01 to 4 parts by weight of a sulfur-containing costabilizer, and optionally of from 0.01 to 3 parts by weight of a basic or neutral metal soap such as, for example, calcium stearate or zinc stearate, and optionally of from 0.1 to 5 parts by weight of a phosphite and optionally of from 0.01 to 5 parts by weight of a known UV-stabilizer of the group of alkoxy-hydroxy-benzophenones, 4-hydroxyphenyl-benzotriazoles, benzylidene-malonic acid-mnonitrile esters or the so-called quenchers, such as nickel chelates.

The following examples illustrate the invention. The molar weight of the polymeric ketones can be derived from the polymeric reduction products.

EXAMPLE 1a

Di-2,2,6,6-tetramethylpiperidin-4-one-3-methane 155 g of 2,2,6,6-tetramethyl-piperidine-4-one in 50 ml of methanol are introduced into a 500 ml apparatus provided with agitator. A solution of 15 g of paraformaldehyde, 2 g of KOH and 80 g of methanol is added dropwise within 5 hours at 60°–70° C. Agitation is continued at this temperature for 24 hours. Subsequently, first the solvent is removed under reduced pressure, and then the residue is distilled under reduced pressure. After having distilled off unreacted 2,2,6,6-tetramethyl-piperidin-4-one, the compound as indicated above is obtained in the form of a red oil.

B.p. 0.4 mbar 180° C.; yield 40 g; molecular weight 330.

EXAMPLE 1b

Reduction of the Ketone 20 g of the compound of Example 1a are dissolved in 100 ml of absolute ether, and the mixture is added dropwise to a suspension of 8 g of lithium aluminum hydride and 100 ml of absolute ether. Subsequently, the batch is refluxed for 10 hours, 20 ml of water are added with cooling, and the solids are extracted several times with hot heptane after having separated the ether. On concentration of the extract, di-2,2,6,6-tetramethyl-piperidine-4-one-3-methane precipitates in the form of crystals, which compound is obtained by filtration.

White solids; m.p. 195°–198° C.

EXAMPLE 2a

Preparation of a Polymer Ketone

Reaction and work-up are as described in Example 1a; however, 1 g of sodium methylate is used as catalyst instead of KOH, and agitation is continued for 26 hours. After having distilled off 90 g of unreacted 2,2,6,6-tetramethyl-piperidone, 56 g of a brittle, dark red resin are obtained.

EXAMPLE 2b

Reduction of the Polymer Ketone

The polymer ketone is dissolved in 200 ml of absolute ethanol, 26.5 g of sodium boron hydride are added, and the batch is agitated for 48 hours at room temperature. Subsequently, the reaction mixture is stirred into 2 liters of water, and the mixture is slightly warmed. After the development of hydrogen is complete, the product is suction-filtered, reprecipitated with methanol/water, and dried.

Yellow powder; softening point 103° C.; molecular weight 3960.

EXAMPLE 3a

Preparation of an Oligomer Ketone 31 g of 2,2,6,6-tetramethyl-piperidin-4-one, 6 g of paraformaldehyde, 0.5 g of KOH powder and 200 ml of n-butanol are refluxed for 65 hours in a 500 ml apparatus provided with agitator. After removal of the solvent, a dark red resin is obtained with quantitative yield.

EXAMPLE 3b

Reduction of the Oligomer Ketone 37 g of the oligomer ketone are dissolved in 200 ml of ethanol, 3.8 g of sodium boron hydride are added, and the batch is agitated for 48 hours at room temperature. Subsequently, about 100 ml of ethanol are distilled off, and the residue is agitated with 500 ml of water (3 hours), the product is then suction-filtered and reprecipitated from methanol/water, thus obtaining 33 g of a yellow product having a melting point of 79°–81° C.

Molecular weight 690.

EXAMPLE 4a

Preparation of an Oligomer Ketone

Preparation and work-up are as described in Example 1 with the use of n-hexanol as solvent, thus obtaining a dark red resin, too.

EXAMPLE 4b

Reduction of the Oligomer Ketone

Reaction and work-up are carried out in analogy to Example 3b using the same amount by weight, thus obtaining 28 g of a product having a melting point of 99°–102° C. and a molecular weight of 670.

EXAMPLE 5a

Preparation of an Oligomer Ketone 155 g of 2,2,6,6-tetramethyl-piperidon-4-one, 30 g of paraformaldehyde, and 2 g of KOH in 400 g of methanol are dissolved in a 2 liter steel autoclave and the batch is heated for 7 hours at 120° C. Subsequently, the solvent is removed, and a dark red resin is thus obtained.

EXAMPLE 5b

Reduction of an Oligomeric Ketone

The resin is dissolved in 500 ml of absolute ethanol, 35 g of sodium boron hydride are added, and stirred for 48 hours at room temperature. The reaction mixture is introduced into 2 liters of water, and stirred for 2 hours. The precipitated solids are suction-filtered, stirred with 500 ml of handwarm water, suction-filtered and dried.

85 g of a yellow powder, m.p. 153° C., molar weight 960.

EXAMPLE 6a

Preparation of a Polymer Ketone

Operations are as in Example 5a; however, with the use of 5 g of NaOH instead of KOH, and with a reaction time of 20 hours. Part of the reaction solution is worked up, thus obtaining a red resin.

EXAMPLE 6b

Catalytic Hydrogenation of the Polymer Ketone 7.0 g of glacial acetic acid are added to the residue of the reaction solution obtained according to Example 6a in order to neutralize the NaOH, and furthermore 30 g of Raney nickel. Subsequently, the batch is hydrogenized at 100° C. and under hydrogen pressure of 150 bars. After 5 hours, the absorption of hydrogen is complete. The reaction solution is suction-filtered with simultaneous recovery of the Raney nickel. The filtrate is stirred into 3 liters of water, whereby the polyalcohol formed precipitates, which is then obtained by filtration.

Molecular weight 1000, m.p. 130°–135° C.

By dissolution in ether, and precipitation with petroleum ether, a fraction having a molecular weight of 1360 (m.p. 160°–170° C.) is obtained.

EXAMPLE 7

Preparation of a Polymer Ketone

A solution of 30 g of paraformaldehyde, 200 ml of methanol and 7.5 g of sodium methylate is added dropwise at 130° C. within 5 hours to a mixture of 155 g of 2,2,6,6-tetramethyl-piperidone and 200 ml of hexanol. The methanol is constantly distilled off. The batch is agitated for a further 20 hours at 130° C., neutralized with glacial acetic acid, the sodium acetate is suction-filtered, and evaporated at 120° C. under reduced pressure. A brittle, orange red resin is obtained on cooling.

Yield: 140 g = 83% of th., m.p. 130°–135° C., molecular weight 690.

EXAMPLE 8

This example demonstrates the light stabilizing action of the compounds of the invention when applying them to a poly-alpha-olefin.

100 parts by weight of polypropylene having a melt flow index i₅ of about 6 g/10 min. (determined according to ASTM D 1238-62 T) and a density of 0.90, were mixed with 0.1 part by weight of pentaerythrityl-tetrakis-[3-(3,3-di-tert.butyl-4-hydroxyphenyl)-propionate], 0.2 part by weight of calcium stearate and 0.1 part by weight of the stabilizer of the invention to be tested. In order to obtain a uniform distribution on the polymer grain, the stabilizers were dissolved in a solvent, and the solution was added dropwise with agitation to the polypropylene powder, while simultaneously radiation by means of an IR lamp ensured substantial evaporation of the solvent. After about 20 minutes, the calcium stearate was added, and the batch was mixed for a further 10 minutes. The solvent remainder was removed by drying in a drying cabinet at 50° C. for 120 minutes.

On a Windsor injection molding machine type SP 50, plates having the dimensions of 60×60×1 mm were molded at 250° C. from the above stabilized plastic mixture, and test specimens according to German Industrial Standard DIN 53 455, form 3, in a scale reduced at a 1:3 ratio, were cut from these plates. The test specimens required as comparative samples were prepared and formed in analogous manner, while omitting either the stabilizer to be tested (test a) or using known light stabilizers (tests b and c).

For testing the stability to light, the specimens were subjected to radiation of changing intensity in a Xenotest 1200 apparatus of the company Original Hanau Quarzlampen GmbH. The radiation intensity was modulated by UV filters (special filter glass d=1.7 mm). The stability to light was tested according to German Industrial Standard DIN 53 387 (17 min. of moistening, 3 min. of sprinkling, black panel temperature 45° C., atmospheric moisture 70–75%). The time of exposure was measured in hours, and the elongation at break was determined on a corresponding testing machine of the company Instron at a draw-off speed of 5 cm/min.

The results are listed in the following Table.

| Test | Stabilizer acc. to Example | Time of exposure |
|---|---|---|
| (a) | Control (without stabilizer) | <345 |
| (b) | benzophenone-stabilizer[1] | <950 |
| (c) | HALS-stabilizer[2] | 950 |
| (d) | 2b | >1000 |
| (e) | 5b | >1000 |

[1] = 2-hydroxy-4-n-octyloxybenzophenone
[2] = bis-2,2,6,6-tetramethylpiperidyl-sebacate

What is claimed is:

1. A process for the preparation of polyalkyl-piperidine/formaldehyde polymers which comprises reacting a polyalkyl-piperidone-4 of the formula (I)

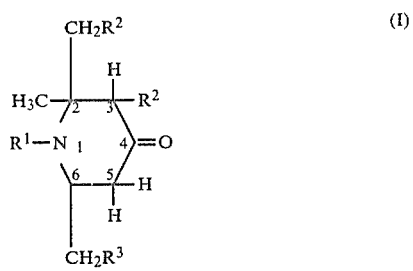

in which
R¹ is hydrogen, oxygen or C₁–C₁₂-alkyl,
R² and R³ are either identical and represent hydrogen or a C₁–C₅-alkyl group,
R⁴ being a methyl group in this case; or
R² is hydrogen or C₁–C₅-alkyl, and
R³ and R⁴ together with the carbon atoms linked to them form a C₅ or C₆ cycloalkyl group, or a group of the formula

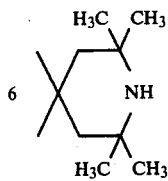

with the 0.5- to 1.1-fold molar amount of paraformaldehyde at a temperature of from 50° to 180° C. in the presence of an aliphatic $C_1$–$C_{10}$-monoalcohol and of an alkaline base, and subsequently optionally hydrogenating the product obtained either completely or partially according to known processes.

2. Polyalkyl-piperidine/formaldehyde polymers of a polymerization degree of from 2 to about 200 and the hydrogenation or partial hydrogenation products thereof, obtained as claimed in claim 1.

3. A process for stabilizing synthetic polymers against the damaging influence of light, which comprises adding to the polymer from 0.01 to 5 parts by weight, relative to the polymer, of a polymer stabilizer as claimed in claim 2, optionally in addition to hitherto known stabilizing substances.

4. Synthetic polymers stabilized against UV decomposition, which contain from 0.01 to 5 parts by weight, relative to the polymer, of a polymer stabilizer as claimed in claim 2.

* * * * *

UNITED STATES PATENT AND TRADEMARK OFFICE
CERTIFICATE OF CORRECTION

PATENT NO. : 4,234,471

DATED : November 18, 1980

INVENTOR(S) : Hartmut Wiezer et al

It is certified that error appears in the above-identified patent and that said Letters Patent are hereby corrected as shown below:

Column 1, lines 26 - 38, the structural formula should read:

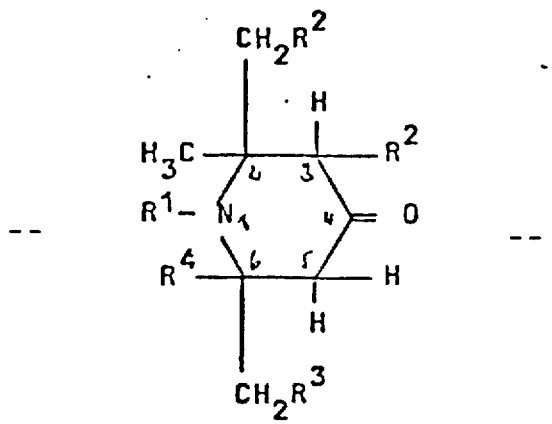

UNITED STATES PATENT AND TRADEMARK OFFICE
CERTIFICATE OF CORRECTION

Page 2 of 2

PATENT NO. : 4,234,471
DATED : November 18, 1980
INVENTOR(S) : Hartmut Wiezer et al It is certified that error appears in the above-identified patent and that said Letters Patent are hereby corrected as shown below:

Column 8, lines 47 - 58, the structural formula should read:

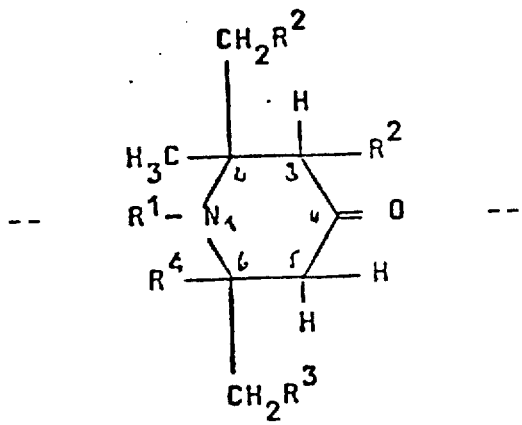

Signed and Sealed this

Tenth Day of March 1981

[SEAL]

Attest:

RENE D. TEGTMEYER

*Attesting Officer*  *Acting Commissioner of Patents and Trademarks*